United States Patent
Kubicek et al.

(10) Patent No.: US 9,352,248 B2
(45) Date of Patent: May 31, 2016

(54) METHOD OF LOADING A CRYSTALLIZATION DEVICE

(75) Inventors: Johann Kubicek, Cologne (DE); Frank Schaefer, Duesseldorf (DE); Joerg Labahn, Korschenbroich (DE); Georg Bueldt, Juelich (DE)

(73) Assignees: QIAGEN GmbH, Hilden (DE); CUBE BIOTECH GmbH, Monheim (DE)

( * ) Notice: Subject to any disclaimer, the term of this patent is extended or adjusted under 35 U.S.C. 154(b) by 1226 days.

(21) Appl. No.: 13/121,359

(22) PCT Filed: Sep. 28, 2009

(86) PCT No.: PCT/EP2009/006964
§ 371 (c)(1),
(2), (4) Date: Jul. 18, 2011

(87) PCT Pub. No.: WO2010/037510
PCT Pub. Date: Apr. 8, 2010

(65) Prior Publication Data
US 2011/0269941 A1    Nov. 3, 2011

(30) Foreign Application Priority Data

Sep. 30, 2008  (EP) .................................... 08017180

(51) Int. Cl.
C30B 29/58    (2006.01)
B01D 9/00    (2006.01)
B01L 3/06    (2006.01)

(52) U.S. Cl.
CPC ................ *B01D 9/00* (2013.01); *B01D 9/0077* (2013.01); *B01L 3/06* (2013.01)

(58) Field of Classification Search
USPC .............................. 117/68, 70, 929, 927, 200
See application file for complete search history.

(56) References Cited

U.S. PATENT DOCUMENTS

2002/0072703 A1  6/2002  Nollert
2003/0150379 A1  8/2003  Goodwin
(Continued)

FOREIGN PATENT DOCUMENTS

EP  1462454     9/2004
JP  2009-69898  4/1997
(Continued)

OTHER PUBLICATIONS

Caffrey, Martin, Membrane Protein Crystallization. Journal of Structural Biology, vol. 142, (2003), pp. 108-132.
(Continued)

*Primary Examiner* — Robert M Kunemund
(74) *Attorney, Agent, or Firm* — Fanelli Haag PLLC (57) ABSTRACT

The present invention pertains to a method for loading a crystallization device and for manufacturing a crystallization device comprising multiple receptacles with a pre-defined amount of at least one matrix-forming compound capable of forming a crystallization matrix for a membrane protein, said method comprising the following steps: a) Modifying the state of aggregation of said at least one matrix-forming compound to a fluidic state which allows dispensing said at least one matrix-forming compound, and b) dispensing a defined amount of said at least one matrix-forming compound into at least one receptacle of the crystallization device, wherein said dispensed matrix-forming compound solidifies within said receptacle. Thereby, pre-filled crystallization devices are obtained which can be used as consumables in particular in automated crystallization processes. Also provided are protein crystallization methods using respectively prepared crystallization devices.

8 Claims, 5 Drawing Sheets

(56) References Cited

U.S. PATENT DOCUMENTS

2006/0099572 A1  5/2006  Kwong
2007/0025895 A1  2/2007  Qin

FOREIGN PATENT DOCUMENTS

| | | |
|---|---|---|
| JP | 2006-83126 | 3/2003 |
| JP | 2004-527606 | 9/2004 |
| JP | 2005-77255 | 3/2005 |
| WO | WO 00/14311 | 3/2000 |
| WO | WO 00/78445 A1 | 12/2000 |
| WO | WO 02/068562 | 9/2002 |
| WO | WO 03/053998 A1 | 7/2003 |
| WO | WO 2006/036772 | 4/2006 |
| WO | WO 2006-098619 A1 | 6/2006 |

OTHER PUBLICATIONS

Cherezov, et al. Membrane Protein Crystallization in Meso: Lipid Type-Tailoring of the Cubic Phase, Biophysical Journal, vol. 83, Dec. 2002, pp. 3393-3407.

Cherezov, et al., Room to Move: Crystallizing Membrane Proteins in Swollen Lipidix Mesophases, Journal of Molecular Biology, vol. 357 (2006), pp. 1605-1618.

Landau et al., Lipidic Cubic Phases: A Novel Concept for the Crystallization of Membrane Proteins, Proc. Natl. Acad. Sci. USA, vol. 93 (1996) pp. 14532-14535.

Journal of Applied Crystallography, "A simple and inexpensive nanoliter volume dispenser for highly viscous materials used in membrane protein crystallization", 2005, vol. 38(2), pp. 398-400.

METHOD OF LOADING A CRYSTALLIZATION DEVICE

This application is a National Application of International Application Number PCT/EP2009/006964 which was filed on Sep. 28, 2009, which claims benefit of European Patent Application No. 08017180.4, filed Sep. 30, 2008, the disclosures of each of which are incorporated herein by reference herein in their entireties.

The present invention pertains to the crystallization of biopolymers, in particular membrane proteins and to automatable methods for loading crystallization devices with matrix-forming compounds.

Three-dimensional protein structures have extremely high commercial value since they allow for the use of rational (structure-based) design and engineering of novel drug molecules that bind to the protein of interest. Furthermore, they facilitate the rational engineering of novel proteins with desired properties. The three-dimensional structure of proteins and other biopolymers is usually determined by X-ray diffraction of the respective crystals. In order to visualize them via X-ray diffraction crystallography, one must grow quality crystals of the biopolymer. Unfortunately, the science of protein crystal growth is currently incapable of predicting the conditions under which a particular protein will crystallize. Thus, as with many other combinatorial problems, one must search a high dimensional parameter space (large number of possible recepies/combinations) to find the optimal crystallization conditions. Often simple screening as many experiments as possible is the most effective method. This is extremely labor-intensive and time consuming. Thus, preparing quality protein crystals remains the bottleneck for elucidating the structure of proteins via X-ray diffraction crystallography. As a result, there has been significant effort to automate this process in order to allow screening many different crystallization conditions.

Membrane proteins are a broad class of proteins which bind to/or traverse a lipid bilayer (membrane) that surrounds all living cells. Membrane proteins are typically involved in the controlled movement of substances and/or signals across the cell membrane. Doing so, membrane proteins enable rapid communication between the inside and outside of living cells. Examples of membrane proteins include ion channels, signaling receptors, hormone receptors, light receptors and adhesion proteins. Such membrane proteins are often the target of drug development and in the centre of scientific attention due to their involvement in signaling processes. One of the defining features of membrane proteins is that both hydrophobic and hydrophilic regions exist on their surfaces. This allows the membrane proteins to blend into the hydrophobic region created by the lipid bilayer of the membrane which makes up most of the membrane and still to have a stable interface with the aqueous material on either side of the membrane. However, these characteristics make it difficult to crystallize membrane proteins by crystallization methods used for soluble (non-membrane bound) proteins, such as the vapor diffusion method. Membrane proteins easily denature and thus loose their structure in aqueous solvents. Therefore, crystallizing membrane proteins is particularly challenging. However, as membrane proteins are coded for by approximately 30% of the genome of all known genomes, their structures are of extremely high interest.

Figure 1:
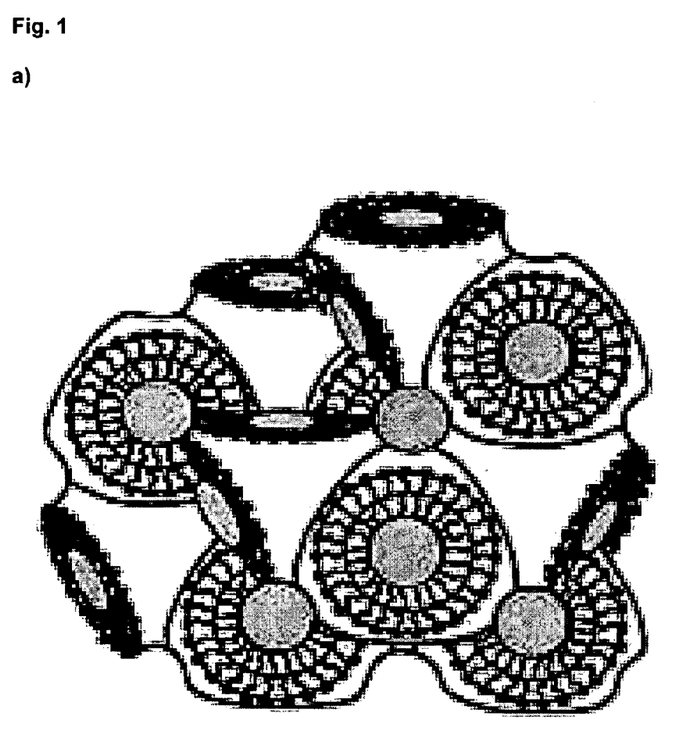

In 1996, Landau and Rosenbusch described the novel use of lipidic cubic phases for the crystallization of membrane proteins. According to this method, the detergent solubilized membrane protein is mixed with a crystallization matrix-forming compound such as monoolein (or monopalmitolein) and water (or buffer solutions), followed by multiple rounds of centrifugation. By this method, a viscous, bi-continuous cubic phase is created, a cured lipid bilayer, extending in three dimensions and permeated by aqueous channels. The matrix-forming compound monoolein is thus capable of forming a crystallization matrix for the membrane proteins, as it provides suitable lipid bilayer structures for the membrane protein. The membrane proteins can partition into the lipid bilayer and can diffuse therein in three dimensions which allow them to explore many potential spatial packing configurations that can lead to crystal growth of the protein within the lipidic meso phases, such as the so called lipidic cubic or sponge phase. An example of a respective lipidic cubic phase is shown in FIG. 1. Respective phases are thus very suitable crystallization matrices for membrane proteins.

Since then, further matrix-forming compounds besides monoolein which are also capable of forming suitable crystallization matrices for a membrane protein were identified and are used for crystallizing membrane proteins.

Still, crystallization of membrane proteins and other polymers remains a challenge. This particularly, as the handling and creation of the crystallization matrix for membrane proteins, such as for example a meso, sponge or cubic phase, are difficult. In particular, it is very time consuming to set up the experiments. Usually, only a few crystallization experiments can be set up in one day by one person. Since large numbers of crystallization conditions are often tested in order to find a lead, such testing methods have been undesirable due to the excessive number of handling steps involved. Furthermore, there is an inherent waste of test material. Since the test material (for example the matrix-forming lipid and the protein) is sacred to begin with, this waste of material often prevents a sufficient number of tests from being conducted.

In the prior art, there are basically two methods used in order to create the crystallization matrices for biopolymers, in particular for membrane proteins. According to one approach, the membrane protein and the matrix-forming compound (for example a lipid such as monoolein) are mixed in an aqueous solution in order form a lipidic cubic phase, wherein the membrane protein is reconstituted in the crystallization matrix (cubic phase) formed by the matrix-forming compound, e.g. monoolein. Said lipidic cubic phase is then transferred to a dispenser. From the dispenser, the lipidic cubic phase is then dispensed into the receptacles of a crystallization device, for example a multi-well plate. Other components necessary for crystallization such as e.g. a precipitating solutions and the like are then added to the dispensed lipidic cubic phase in order to initiate the crystallization process. This method is for example described in U.S. 2002/0072703. This method, however, requires large amounts of proteins in order to set up the "master mix" of protein and matrix-forming lipidic compound in order to form the crystallization matrix (e.g. the cubic phase) prior to dispension, that are regularly not obtainable. A further drawback of this approach is that it is not possible for example to vary the nature of the matrix-forming compound in order to find the optimal matrix-forming compound for the particular protein of interest as the protein is pre-mixed with the matrix-forming compound. Thus, it is either necessary to prepare several "master mixes" of protein and lipidic cubic phase—what is protein consuming—or it is not possible to vary the matrix-forming compound. Furthermore, mixing of the membrane protein and the lipidic matrix-forming compound must be performed e.g. manually by the user. Dispensing the respectively created cubic phase is difficult due to the viscous nature of the cubic phase and thus also time consuming or at least error-prone.

A further problem is that the effect of the precipitating solution on the cubic phase and on the protein can not be controlled separately, since the mixture of cubic phase and protein is contacted with the precipitating solution. Different types of precipitants induce different changes of the cubic phase. This may be interesting to analyze before contacting the cubic phase with the membrane protein solution. Therefore, the current methods of combining first the matrix-forming compound and the protein limit the screening possibilities for an ideal combination of matrix-forming compound, membrane protein and precipitating solution.

A different approach employs the manual preparation of the matrix-forming compound by weighing very small amounts of the pure matrix-forming compound into the receptacles of a crystallization device, such as e.g. a multi-well plate. The protein solution is then added to the prepared matrix-forming compound in order to induce the formation of the crystallization matrix. In this respect it is very important to mix the matrix-forming compound with the membrane protein in an exact proportion/concentration. Therefore, the amount of matrix-forming compound contained in the receptacle of the crystallization device must be as exact/defined as possible. This is difficult though, as the matrix-forming compounds are usually solid compounds due to their lipidic nature. Respective solid compounds which often exist in a flakey condition, such as the monoolein, are difficult to be weighed and this is also a very time consuming procedure, considering that possibly hundreds or even thousands of different conditions should ideally be screened in one crystallization experiment. Therefore, individually weighing defined amounts of matrix-forming compound is not suitable for medium or high throughput crystallization experiments. Furthermore, as providing an exact proportion of cubic phase and membrane protein is essential for an ideal and reproducible crystallization experiment, the weighing process is also error prone.

To identify ideal crystallization conditions and optimize crystallization processes there are still many improvements that need to be made, especially when only small amounts of protein are available. There is thus a great need for automatable processes in this field of science in order to allow medium and high throughput screenings of crystallization conditions.

According to a first embodiment of the present invention a method for loading a crystallization device comprising multiple receptacles with a pre-defined amount of at least one matrix-forming compound capable of forming a crystallization matrix for a membrane protein is provided, comprising the following steps:
  a) Modifying the state of aggregation of said at least one matrix-forming compound to a fluidic state which allows dispensing said at least one matrix-forming compound, and
  b) dispensing a defined amount of said at least one matrix-forming compound into at least one receptacle of the crystallization device, wherein said dispensed matrix-forming compound solidifies within said receptacle.

Matrix-forming compounds capable of forming a crystallization matrix for a membrane protein (herein also referred to as "matrix-forming compound") are usually solid at room temperature (see above). Therefore, the prior art weighs the individual amounts of the solid compound into the receptacles. As is outlined above, this is time consuming, error-prone and thus not suitable for an automated process. The present invention departs from that approach and modifies the state of aggregation of said matrix-forming compound to a fluidic state, which allows dispensing said at least one matrix-forming compound into the receptacles of the crystallization device. For example, depending on the used dispenser, it is sufficient if the state of aggregation is modified such that the matrix-forming compound exists in a viscous (or liquid) and therefore dispensable state of aggregation. Thereby, it is possible to dispense a defined amount of said at least one matrix-forming compound into the receptacles of the crystallization device. The respective process is also automatable, as the fluidic matrix-forming compound can be dispensed in exact proportions/amounts. So far, no method exists in the prior art to provide multiple small but exact amounts of matrix-forming compound for the crystallization of biopolymers, in particular for membrane proteins.

Said matrix-forming compound solidifies within said receptacle after being dispensed. Therefore, a crystallization device is obtained from the loading method according to the present invention, comprising exact amounts of matrix-forming compounds in a solid state, which can therefore be provided to the user as a storable, ready-to-use consumable. The user e.g. only needs to add the protein to be crystallized to the matrix-forming compound contained in the receptacle e.g. in form of a protein solution, whereby the crystallization matrix comprising the protein/biopolymer to be crystallized is spontaneously formed (also two step procedures are feasible, wherein first water or a buffer is added to form the crystallization matrix and the protein to be crystallized, see below). Afterwards, the precipitating solution(s) can be added in order to initiate the crystallization process. By using the crystallization device loaded according to the method of the present invention, it is not necessary for the consumer to load the crystallization device himself with the matrix-forming compound/crystallization matrix which is problematic (see above). Only the protein to be crystallized and the other components/solution necessary for crystallization need to be added by the end user as is described below. However, as the respective components are easy to dispense (e.g. the protein and/or the precipitating solution), this also allows the performance of the crystallization experiment in a medium or high throughput format. This will be explained in further detail in conjunction with the crystallization method.

Furthermore, the method according to the present invention allows to load the receptacles of the crystallization device with different matrix-forming compounds or mixtures of matrix-forming compounds, thereby providing more flexibility compared to methods of the prior art wherein e.g. the matrix-forming compound is premixed with the protein in order to form the cubic phase prior to the dispensing process. Furthermore, dispensing the cubic phase—which needs to be done manually according to prior art methods—is difficult and thus inconvenient for the user. The method according to the present invention for loading a crystallization device is automatable and therefore suitable for preparing prefilled crystallization devices for high throughput screens. The storable pre-filled crystallization devices can also be used in conjunction with robotic systems, which dispense the further components (e.g. proteins and precipitating solutions) to set up the medium or high throughput screens.

The present invention thus provides important advantages over conventional loading methods as it provides storable, ready-to-use pre-filled crystallization devices that provide the user with the highest amount of flexibility and convenience.

The method according to the present invention departs from the prior art methods in that the crystallization matrix is not formed prior to the dispensing step. In particular, the matrix-forming compound is not mixed with the biopolymer to be crystallized prior to the dispensing step. Therefore, the crystallization device comprising the solidified, defined amounts of matrix-forming compound can be stored and therefore be provided to the user as ready-to-use consumables. Methods, wherein the crystallization matrix is dispensed and thus pre-filled, e.g. as a cubic or sponge phase, can only be stored for a short time (probably not more than a few months) as the crystallization matrix is fragile and easily collapses e.g. due to dehydration. These problems do not arise with a crystallization device loaded according to the method of the present invention, as the solidified matrix-forming compound is more robust and can thus be stored even for years under appropriate storage conditions.

The crystallization device can be for example a protein crystallization plate. Respective plates are usually provided in a multi well format, for example comprising $3 \times 2^N$ wells with N being a natural number, like 24, 96 and potentially 384 wells. Several designs of crystallization devices are known in the prior art and can be used according to the present invention.

The method of the present invention can also be incorporated/performed as integral component/step of a robotic station, which not only loads the crystallization devices with said at least one matrix-forming compound, but which also adds for example the protein solutions and the other necessary solutions/ingredients for the crystallization process (for example a precipitating solution).

The crystallization device can be for example a protein crystallization plate which allows the crystallization of biopolymers, in particular membrane proteins, via the sitting or hanging drop vapor diffusion method. For this purpose, according to one embodiment the protein crystallization plate may comprise at least one receptacle for receiving the at least one matrix-forming compound capable of forming a crystallization matrix for a membrane protein and additionally, at least one reservoir which is in communication with said at least one receptacle. Said communication may be e.g. gaseous such as in vapor diffusion methods. However microdialysis approaches employing semipermeable membranes are also feasible. Said reservoir, for example, can be filled with a precipitating solution in order to promote the crystallization process, respectively to allow for screening more crystallization conditions. It is also possible that several receptacles for the matrix-forming compound are in gaseous communication with at least one reservoir (see for example WO 00/14311). A respective embodiment is advantageous if e.g. the receptacles in gaseous communication with said at least one reservoir are loaded/pre-filled with different matrix-forming compounds or mixtures of matrix-forming compounds as the variability of the screening experiment can be increased thereby.

According to one embodiment, the state of aggregation of said at least one matrix-forming compound is modified by modifying the temperature of said matrix-forming compound prior to or during the dispensing step in order to reach the fluidic state allowing dispensing the matrix-forming compound. For example, most matrix-forming compounds are lipidic compounds which are solid at room temperature. However, by heating the respective matrix-forming compounds they reach a fluidic state, wherein the compounds are for example either liquid or at least viscous, which allows dispensing defined amounts into the receptacles of the crystallization device. The temperature that must be obtained respectively maintained for dispension depends on the matrix-forming compound or composition of matrix-forming compounds used and may be determined easily by testing at which temperature a fluidic state is reached, which allows dispensing said at least one matrix-forming compound or composition into the receptacles of the crystallization device. For lipidic matrix-forming compounds such as monoolein, temperatures above 30° C. and preferably above 40° C. (e.g. around 42° C.) are usually sufficient in order to reach a fluidic state which allows dispensing said compounds into the receptacles of the crystallization device. However, also higher temperatures may be used. According to one embodiment, approximately 100 nl to 1000 nl, or less than 500 nl of matrix-forming compound is dispensed. However, also larger volumes may be dispensed depending on the intended application and design of the crystallization plate.

Preferably, said loading method is automated by using a robotic system comprising at least one dispensing unit for dispensing said at least one matrix-forming compound. In case the state of aggregation is modified by heating the matrix-forming compound, the tip or any other part of the dispenser may be used for setting the matrix-forming compound to a temperature which allows dispensing defined amounts of said material. It is also possible to for example warm the matrix-forming compound within the dispenser by an external heating process (for example by blowing hot air) in order to reach the necessary temperature allowing dispensing said at least one matrix-forming compound into the receptacles of the crystallization device. Accordingly, according to one embodiment said at least one matrix-forming compound is heated in the dispensing unit e.g. of a robotic system. The term "dispenser" or "dispensing unit" is used herein for a device, which allows dispending defined amounts of a fluidic, e.g. a liquid or viscous substance. If small volumes shall be dispensed, the dispenser should be suitable for dispensing very small but exactly defined amounts of liquid and/or viscous substances, especially in a µl or nl volume range.

Preferably, said matrix-forming compound has at least one of the subsequent characteristics.

As is outlined in the introduction, respective matrix-forming compounds are suitable for forming a crystallization matrix for a membrane protein e.g. upon hydration. In order to be capable of forming a crystallization matrix for a membrane protein, it is important that the matrix-forming compound is capable of forming a structure which mimics the lipidic bilayer of a biomembrane in order to allow the incorporation of the membrane protein into said structure mimicking the lipidic bilayer of biomembranes. Compounds, which are suitable for that purpose, are in particular lipidic compounds, preferably amphiphilic compounds and in particular alcohol derivatives from fatty acids. Respective compounds usually comprise a saturated or unsaturated fatty-acid chain as lipidic component. The chain length may vary from 14 to 25 carbons, more preferably from 16 to 20 or 16 to 18 carbons which closely resemble natural lipids.

Suitable crystallization matrices known in the prior art are e.g. the meso phase, the cubic phase and/or the sponge phase. The boundaries between the respective phases/crystallization matrices are not distinct. E.g. the term "meso phase" is often used as generic term encompassing the cubic and the sponge phase (for details see e.g. Caffrey et al, Journal of Structural Biology 142 (2003) 108-132, Cherezov et al, Biophysical Journal Volume 83 December 2002 3393-3407, Cherezov et al, J. Mol. Biol. (2006) 357, 1605-1618, all herein fully incorporated by reference). As is outlined in these documents, the transitions between the individual phases (including the cubic and the sponge phases) are fluent and may even vary for a particular matrix-forming compound, e.g. depending on the temperature, additives and/or water content. E.g. the swelling of a cubic phase by using a higher proportion of water and/or additives has the effect that the cubic phase looses its ordered structure while retaining a bicontinuous character and transforms into what is referred to as sponge phase (please also refer to FIG. 1). A respective swelling can be e.g. beneficial if larger proteins are supposed to be crystallized, as the lattice parameter of the crystallization matrix is increased.

As is outlined above, said matrix-forming compound can be used alone or in combination with a further matrix-forming compound also capable of forming a crystallization matrix for a membrane protein. A respective mixture allows testing different crystallization matrices for different proteins, which allows the optimization and fine tuning of the crystallization conditions for the biopolymer to be crystallized. It is important to understand, that depending on the structure and the size of the biopolymers, in particular membrane proteins, different matrix-forming compounds may lead to different crystallization results. Therefore, it is also advantageous, to load the receptacles with different matrix-forming compounds or mixtures of matrix-forming compounds in order to vary and optimize this parameter. This flexibility is an important advantage.

Additionally or alternatively, it can also be advantageous to mix the matrix-forming compound(s) with a further additive in order to further alter/adapt the crystallization matrix for the biopolymer to be crystallized. Respective additives may support the formation of crystals, as they may have the effect that the biopolymer to be crystallized finds better conditions/surroundings, preferably due to the addition of a respective lipidic additive. The mixture of the matrix-forming compound(s) and the additive form an additive composition which is still capable of forming a crystallization matrix for a membrane protein. Respective additives may be lipidic, long-chain alcohols or natural or synthetic components that may stabilize the membrane protein in the crystallization matrix. Respective additives may be added to the matrix-forming compound or could be added by the user when adding the components for forming the crystallization matrix (e.g. the protein solution or a solution comprising optionally additives for altering the crystallization matrix).

Said matrix-forming compound or said additive composition consists of or comprises at least one compound selected from the group consisting of
  a) Fatty acids, alcohol derivatives from fatty acids, monoglycerides, diglycerides, lipids and their derivatives, preferably the corresponding compounds that have their acid group(s) replaced by a hydroxyl or thiol or ether or thioether group or ω-hydroxyalkenes or their ethers or homologous thiols or thioethers; monoacylglycerols, preferably cis monounsaturated monoacylglycerols, more preferably monoolein (C18: c9), monopalmitolein (C16: c9) and monovacennin (C18: c7); medium-chain length alkyl glycosides; polyalkylengylcols, polyethylenglycols, diacylglycerophospholipids, monoacylglycerophospholipids and derivatives thereof capable of forming a crystallization matrix for a biopolymer; and/or
  b) polyketides, saccharolipids, prenol lipids, sterol lipids, sphingolipids, glycerophospholipids and glycerolipids and/or derivates of lipids, in particular phosphatidylcholine (PC), in particular 1,2-dioleyl-sn-glycero-3-phosphocholine (DOPC), phosphatidylethanolamine, in particular 1,2-dioleyl-sn-glycero-3-phosphoethanolamine (DOPE), phosphatidylserine, in particular 1,2-dioleyl-sn-glyero-3-phosphoserine (DOPS), cardiolipin, lysophosphatidylcholine, 2-monoolein, oleamide, cholesterol, cell membrane components, and natural or synthetic compounds stabilizing the membrane protein in the crystallization matrix.

Thus, many suitable matrix-forming compounds exist that can be used in conjunction with the present invention either alone, as mixtures and/or in combination with the listed additives.

Also provided is a method for manufacturing a respective pre-filled crystallization device by using the method according to the present invention.

Also provided with the present invention is a crystallization device comprising multiple receptacles, wherein at least some of said receptacles comprise a defined homogenous amount of at least one solid matrix-forming compound capable of forming a crystallization matrix for a membrane protein. Homogeneous in this respect means that the matrix forming compound is not in a flakey state but forms a homogeneous drop/structure in the receptacle. E.g. a respective homogenous structure can be achieved, if said at least one matrix-forming compound was dispensed into said receptacles in a fluidic state of aggregation and solidified within said receptacle by using the method according to the present invention.

The advantages of modifying the state of aggregation to a fluidic state which allows dispensing said at least one matrix-forming compound is discussed above in detail in conjunction with the loading method. We thus refer to the above disclosure. Preferably, the state of aggregation is modified by heating the matrix-forming compound. Upon dispensing the matrix-forming compound into said receptacles, said compound solidifies again within said receptacle when it cools down at least to room temperature. It is also possible to promote that process by cooling or freezing the loaded crystallization device.

A crystallization device prepared according to the teachings of the present invention can be distinguished from devices wherein portions of the solid matrix-forming compound were weighed into the receptacles in a solid state or devices comprising the hydrated crystallization matrix due to its homogeneous structure. E.g. if the matrix-forming compound is dispensed in a fluidic state according to the present invention and solidifies within the receptacle, said matrix-forming compound is homogenously distributed within said receptacle and can be stored for a long time.

The crystallization devices e.g. may be sealed in order to protect the matrix-forming compound from hydration and accordingly may be prepared for storage until the crystallization devices are contacted with the hydration and/or protein solutions and optionally other components for the crystallization experiment. It is an advantageous feature that only the matrix-forming compound and optionally additives capable of forming a crystallization matrix are preloaded within the receptacles of the crystallization device, as the solid matrix-forming compound can be stored over a long term period (see above). This is for example not possible with pre-mixed or pre-formed crystallization matrices such as cubic or sponge phases, which do not have a solid structure and easily dehydrate and thus collapse during storage. The prior art methods which dispense the pre-formed crystallization matrix (e.g. the cubic or sponge phase) are thus not suitable for long term storage and are more difficult to handle/store due to their susceptibility. Furthermore, depending on the biopolymer to be crystallized, it may also be of interest for the user to vary the liquid used for hydration of the matrix-forming compound and thus for the creation of the crystallization matrix, in order to further increase the combinatorial flexibility and thus the chance to find ideal crystallization conditions.

Therefore, the crystallization devices according to the present invention have important advantages over the prior art devices, as they provide storable, ready-to-use consumables which provide a high flexibility for high throughput screening experiments. Furthermore, as outlined above, they can also be used in conjunction with robotic systems performing or setting up the whole crystallization experiments, from the loading of the crystallization devices with the at least one matrix-forming compound according to the present invention, over the addition of the protein solution and the precipitating solution, the sealing and storage of the prepared crystallization devices for crystallization.

Thus, an advantageous feature of the crystallization device of the present invention is that said at least one matrix-forming compound that was e.g. dispensed in a fluidic state and solidified within the respective receptacle, was not pre-mixed with a biopolymer to be crystallized prior to the dispensing step and/or was not dispensed as crystallization matrix such as, e.g. as cubic or sponge phase, as respective crystallization matrices are less stable than the matrix-forming compound which has not yet formed the crystallization matrix, or mixture/composition thereof optionally mixed with additives as described above. A respective crystallization matrix is then formed, when the user adds the necessary components, such as water and/or a protein solution.

According to one embodiment, the crystallization device is a protein crystallization plate. Preferably, the plate is present in a multi-well format. Suitable crystallization devices and suitable embodiments thereof were described in detail above; we refer to the above disclosure.

According to one embodiment, said matrix-forming compound capable of forming a crystallization matrix for a membrane protein has at least one of the following characteristics:
  a) It is capable of forming a meso phase; and/or
  b) It is capable of forming a cubic phase; and/or
  c) It is capable of forming a sponge phase; and/or
  d) It is lipidic; and/or
  e) It is amphiphilic; and/or
  f) It comprises a saturated or unsaturated fatty-acid chain; and/or
  g) It is an alcoholic derivative from fatty acid.

Further details regarding these compounds, suitable mixtures and compositions comprising additives are discussed in detail above in conjunction with the loading method and equally apply to the matrix-forming compound or matrix-forming composition comprised in the crystallization device according to the present invention. We refer to the above disclosure.

According to a further embodiment, said matrix-forming compound capable of forming a crystallization matrix for a membrane protein is used in combination with a further matrix-forming compound capable of forming a crystallization matrix for a membrane protein and/or is mixed with at least one additive, thereby forming an additive composition. Details regarding respective compositions are outlined in detail above and equally apply to the crystallization device according to the present invention.

According to one embodiment, said matrix-forming compound or said additive composition consists of or comprises at least one compound selected from the group consisting of
a) Fatty acids, alcohol derivatives from fatty acids, monoglycerides, diglycerides, lipids and their derivatives, preferably the corresponding compounds that have their acid group(s) replaced by a hydroxyl or thiol or ether or thioether group or ω-hydroxyalkenes or their ethers or homologous thiols or thioethers; monoacylglycerols, preferably cis monounsaturated monoacylglycerols, more preferably monoolein (C18: c9), monopalmitolein (C16: c9) and monovacennin (C18: c7); medium-chain length alkyl glycosides; polyalkylenglycols, polyethylenglycols, diacylglycerophospholipids, monoacylglycerophospholipids and derivatives thereof capable of forming a crystallization matrix for a biopolymer; and/or
b) polyketides, saccharolipids, prenol lipids, sterol lipids, sphingolipids, glycerophospholipids and glycerolipids and/or derivates of lipids, in particular phosphatdtylcholine (PC), in particular DOPC, phosphatidylethanolamine, in particular DOPE, phosphatidylserine, in particular DOPS, cardiolipin, lyso-phosphatidylcholine, 2-monoolein, oleamide, cholesterol, cell membrane components, and natural or synthetic compounds stabilizing the membrane protein in the crystallization matrix.

The invention also pertains to the use of a crystallization device as described above or a crystallization device produced according to the loading method described above in a method for crystallizing biopolymers, in particular membrane proteins. The advantages regarding the possibility of automating and the flexibility for testing different screening conditions are outlined in detail above. We refer to the above disclosure.

The invention also pertains to a method of crystallizing biopolymers, wherein a defined amount of at least one matrix-forming compound capable of forming a crystallization matrix for a membrane protein contained in at least one receptacle of a crystallization device as described above or a crystallization device manufactured/loaded according to the method described above is contacted with a liquid to form a crystallization matrix, e.g. a meso phase, a cubic phase or a sponge phase.

As is outlined above, the matrix-forming compounds that can be used in conjunction with the present invention, in particular lipidic matrix-forming compounds (see above) spontaneously form a crystallization matrix with resembles/mimics the lipidic bilayer of a biomembrane when contacted with a liquid, in particular an aqueous liquid. Said crystallization matrix is preferably selected from the group comprising meso phases, cubic phases and sponge phases as are well known in the state of the art. Several different suitable crystallization matrices are described above and are also known in the prior art (see e.g. M. Caffrey, Journal of Structural Biology 142 (2003) 108-132; V. Cherezov "Room to Move: Crystallization Membrane Proteins in Swollen Lipidic Mesophases" J. Mol. Biol. (2006) 357, 1605-1618).

It was surprisingly found, that there are alternative routes in order to create the crystallization matrix from the matrix-forming compound. E.g. the ratio of matrix-forming compound to liquid is a determinant for the kind of crystallization matrix that is formed. E.g., if the liquid proportion is higher, a sponge phase is formed rather than a cubic phase. Thus, one may vary the nature of the crystallization matrix not only by e.g. choosing different matrix-forming compounds or mixtures thereof, but also by choosing different hydration conditions in order to form the crystallization matrix from the matrix-forming compound. Usually, the crystallization matrix-forming process takes at least 0.5 to 3 hours. However, this depends on the matrix-forming compound used and the composition of the hydration solution.

According to one embodiment, the protein solution, which usually comprises a detergent, is added to the matrix-forming compound/composition contained within the receptacle of the crystallization device. If the protein solution is aqueous, the crystallization matrix will form spontaneously when incubating the protein solution together with the matrix-forming compound. This procedure has the advantage, that the crystallization matrix, for example the cubic or sponge phase, is formed in the presence of the protein. Thus, the biopolymer to be crystallized, usually a membrane protein, is directly reconstituted and integrated in the crystallization matrix structure which usually resembles/mimics a biomembrane structure (see above). The protein solution may comprise additives, as described above.

According to another embodiment, the matrix-forming compound present in the receptacle of the crystallization device according to the present invention is contacted with an aqueous liquid which does not comprise yet the biopolymer to be crystallized. It was shown, that upon addition of an aqueous liquid (e.g. water and/or a buffer solution), which may e.g. comprise additives, such as lipidic additives, the crystallization matrix is formed very quickly, usually within less than an hour or even within 0.5 hours (see also FIG. 2). The respectively pre-swollen crystallization matrix is then contacted with the protein solution in order to form the crystallization matrix incorporating the protein. The biopolymer is integrated into the crystallization structures mimicking/resembling a biomembrane upon contact by diffusion.

Suitable additives that may be comprised in the aqueous solutions for forming the crystallization matrix can be selected from the group consisting of polyketides, saccharolipids, prenol lipids, sterol lipids, sphingolipids, glycerophospholipids and glycerolipids and/or derivates of lipids, in particular phosphatidylcholine (PC), in particular DOPC, phosphatidylethanolamine, in particular DOPE, phosphatidylserine, in particular DOPS, cardiolipin, lyso-phosphatidylcholine, 2-monoolein, oleamide, cholesterol, cell membrane components, and natural or synthetic compounds stabilizing the membrane protein in the crystallization matrix.

The crystallization matrix may be contacted with a precipitating solution in order to initiate the crystallization process. E.g. upon the addition of a precipitant of suitable composition, changes occur in the crystallization matrix and/or the protein that facilitate protein-protein contacts and stable nuclei formation for inducing the crystal formation. Thus, preferably a precipitating solution is added when the protein is incorporated in the crystallization matrix. Preferably, said crystallization matrix is covered with a precipitating solution, which may be diluted. Thereby, a sponge phase may be created which also serves as a crystallization matrix and which also promotes the crystallization of the incorporated protein. Suitable precipitating solutions are known in the prior art and may e.g. comprise salts, polyalkylenglycols, in particular polyethylenglycol, organic compounds, alcohols and combinations thereof as precipitant.

The crystallization device used may comprise at least one receptacle for receiving the at least one matrix-forming compound capable of forming a crystallization matrix for a membrane protein and at least one reservoir which is in communication with said at least one receptacle. Details of respective designs are described above and apply here as well. Said reservoir can be filled with a precipitating solution, which preferably comprises a higher precipitant concentration than the precipitating solution that is used in order to cover the crystallization matrix (see above).

According to a further embodiment, the precipitating solution in the reservoir is covered with a cover, e.g. a film preventing evaporation. Suitable compounds are non-volatile compounds which are insoluble in water and have a density smaller than water. Suitable materials are for example oil and compounds having a low density. Thereby, the crystallization process is promoted very mildly.

The present invention also provides a screening system for identifying crystallization parameters, in particular for identifying optimum matrix-forming compounds, mixtures thereof and mixtures with additives, by preparing and using a crystallization device according to the present invention. The crystallization reaction of biopolymers, in particular membrane proteins can be tested systematically with this screening system. Due to the pre-dispensed matrix-forming compound, which can also be varied as described above in order to test different crystallization matrices, the user only needs to dispense the desired proteins and precipitating solutions, which are both easily dispensable. The screening system may therefore be used in a wholly automated system, allowing high throughput assays and the fast screening for ideal crystallization conditions.

The invention is subsequently illustrated by way of non-limiting examples.

FIGURES/EXAMPLES

FIG. 1a) is a schematic model of a bicontinuous cubic phase composed of monoolein, water, and a membrane protein as an example of a crystallization matrix. The matrix consists of two compartments, a membrane system with an infinite three-dimensional periodic minimal surface (shown as circular lipidic bilayer), interpenetrated by a system of continuous aqueous channels. The membrane protein is reconstituted into the lipidic bilayer (see also FIG. 1b). A sponge phase has a similar structure as a cubic phase, however, due to the higher water/liquid content, the structure is more open/loose.

FIG. 1b) is a schematic representation of the crystallization process in cubic phases, taken from the prior art (Martin Caffrey, Journal of Structural Biology, 142 (2003) 108-132, see FIG. 13). The general process for crystallizing membrane proteins is the solubilization of the membrane proteins in detergent in an aqueous medium. The detergent forms micelles and also solubilizes the protein in the aqueous medium. When the solubilized proteins in the aqueous medium are contacted with the matrix-forming compound, for example lipids like monoolein, the hydration of monoolein forms contiguous L-alpha and cubic phases (for a description of the phases please also refer to Cherezov et al, J. Mol. Biol. (2006) 357, 1605-1618, FIG. 1). The matrix-forming compound forms membrane-like structures which reconstitute and accordingly incorporate the protein to be crystallized. During the formation of the crystallization matrix, e.g. the shown cubic phase, the protein is reconstituted and dispersed in the crystallization matrix. Thereby, the protein is reconstituted and incorporated in the bilayer of the crystallization matrix, here a cubic phase. The addition of precipitant (e.g. salt) to initiate crystallization by water withdrawing and charge screening effects, induces the crystallization process. The bilayer curvature in the cubic phase increases as water content drops. FIG. 1c) demonstrates the reversible crystallization of the protein (and the lipid, in the case of co-crystallization) from the cubic phase to lamellar type structures. The respective crystallization often takes place via the so-called sponge phase, where the ordered structure of the cubic phase is loosened, before lamellar type structures are formed.

Generally, the processes of protein crystallization in respective crystallization matrixes such as cubic, meso or sponge phases are not completely understood/evolved. Therefore, FIG. 1c) only represents one model system.

Figure 2:
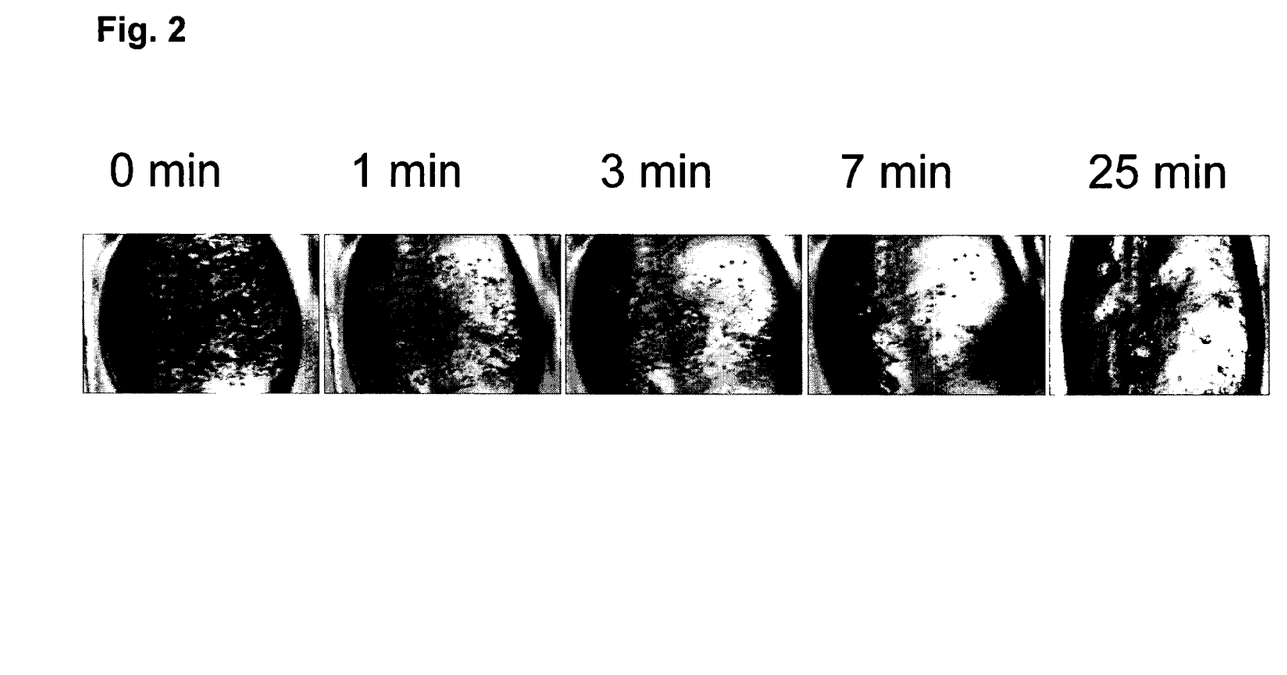

FIG. 2 shows a matrix-forming compound, again monoolein, which was dispensed according to the present invention in a fluidic state. As can be seen, the solidified monoolein is incorporated as a rather homogenous nugget in the receptacle of the crystallisation device. Upon contact with a liquid (here water) the monoolein quickly swells and forms the crystallisation matrix.

Figure 3:
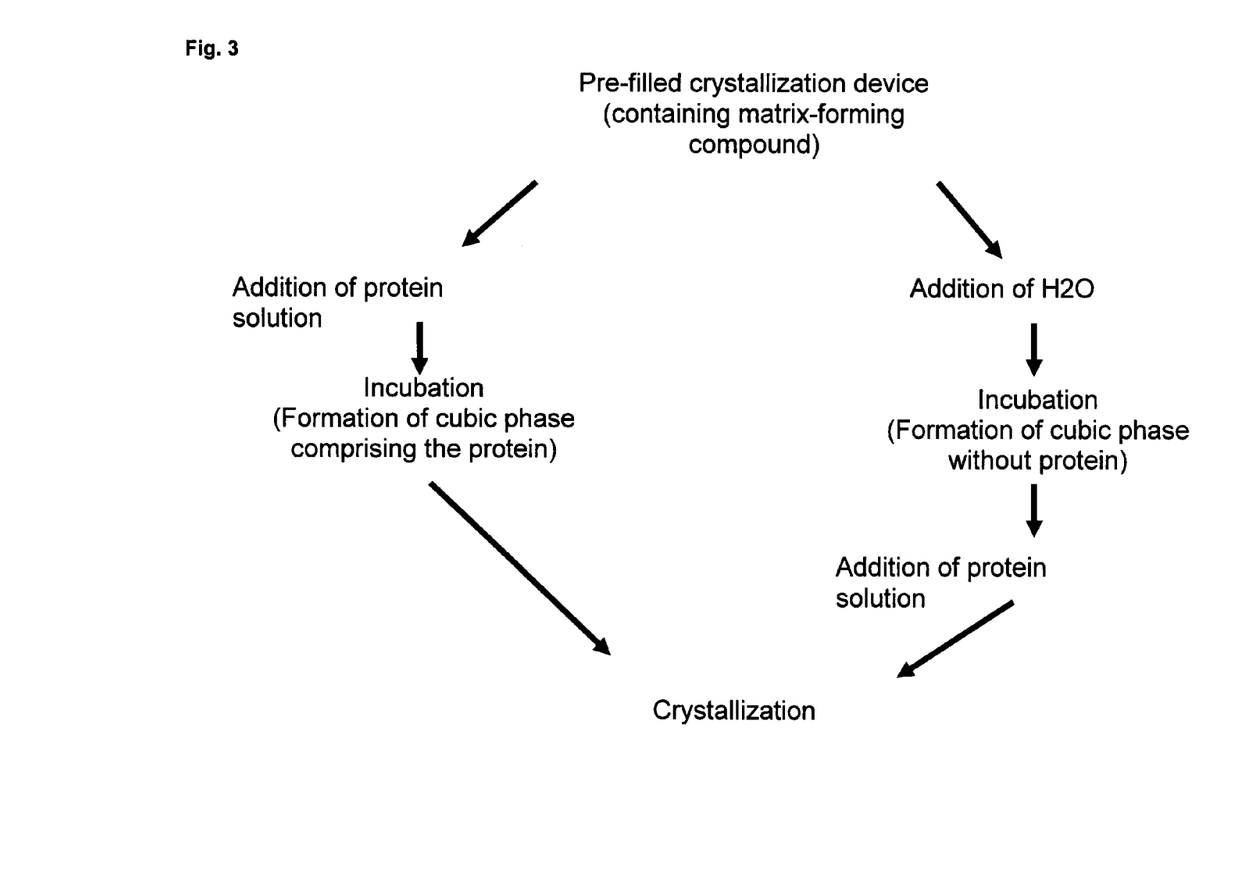

FIG. 3 shows in a practical application flow, how the prefilled crystallization devices according to the present invention can be used in a crystallization experiment. On the left side, the protein solution is added directly to the matrix-forming compound, e.g. monoolein, and a swelling of the matrix-forming compound occurs during an incubation step of approximately 2 to 3 hours to create the crystallized matrix (cubic phase), which comprises the reconstituted protein. On the right side, a different option is shown, wherein a liquid not containing the biopolymer to be crystallized, e.g. water optionally mixed with lipids or other additives, is added to the matrix-forming compound. Swelling of the matrix-forming compound occurs in an incubation step of approximately 30 min to create the crystallization matrix (cubic phase), which does not yet comprise the protein to be crystallized. This short time is usually sufficient in order to swell the matrix-forming compound and to create the crystallization matrix, here the cubic phase. The protein solution is then added to the pre-swollen crystallisation matrix, e.g. a cubic phase. The entry of the protein into the cubic phase occurs passively by diffusion.

Figure 4:
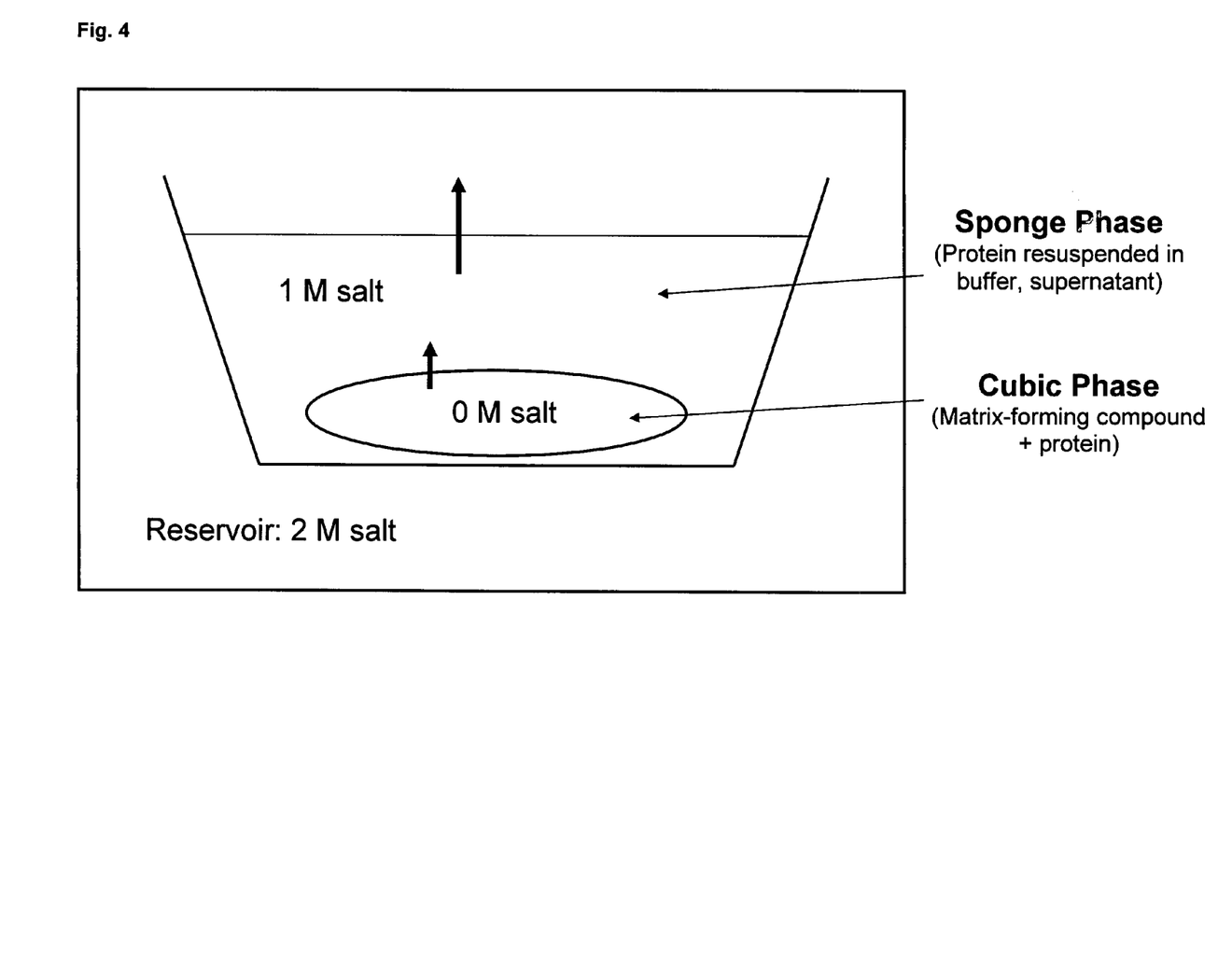

FIG. 4 shows a set up for a membrane protein crystallization experiment using vapour diffusion. The cubic phase (shown in the middle) is covered with a 1M salt solution, which is a diluted precipitating solution. In gaseous communication with said receptacle, a reservoir is provided in the crystallization device, which contains a 2M salt solution, which according to the shown embodiment presents the undiluted precipitating solution. The crystallization occurs via vapour diffusion. The 1M salt solution withdraws water from the cubic phase, while the 2M salt solution in the reservoir withdraws water from the 1M salt solution. Thereby, the water withdrawal occurs very gently and slowly, which provides ideal conditions for the protein (bacteriorhodopsin—BR) to crystallize. According to one embodiment, the liquid present in the reservoir is covered by a protective film, which prevents evaporation from the precipitating solution within the reservoir.

The invention claimed is:

1. A method for loading a crystallization device comprising multiple receptacles with a pre-defined amount of at least one matrix-forming compound capable of forming a crystallization matrix for a membrane protein, comprising:
    a) modifying the state of aggregation of said at least one matrix-forming compound from a solid to a fluidic state which allows dispensing said at least one matrix-forming compound;
    b) dispensing a defined amount of said at least one matrix-forming compound into at least one receptacle of the crystallization device, wherein the at least one matrix-forming compound does not comprise the membrane protein; and
    c) solidifying said at least one matrix-forming compound in said receptacle to form a solidified matrix-forming compound, wherein the solidified matrix-forming compound does not comprise the membrane protein and has not formed a crystallization matrix.

2. The method according to claim 1, wherein the state of aggregation of said at least one matrix-forming compound is modified by modifying the temperature.

3. The method according to claim 1, wherein dispensing said at least one matrix-forming compound into at least one receptacle is automated by using a robotic system comprising at least one dispensing unit.

4. The method according to claim 1, wherein said at least one matrix-forming compound:
    a) is capable of forming a meso phase; and/or
    b) is capable of forming a cubic phase; and/or
    c) is capable of forming a sponge phase; and/or
    d) is a lipidic compound; and/or
    e) is amphiphilic; and/or
    f) comprises a saturated or unsaturated fatty-acid chain; and/or
    g) is an alcohol derivative from a fatty acid.

5. The method according to claim 1, wherein:
    a) said at least one matrix-forming compo is mixed with an additive thereby forming an additive composition; and/or
    b) said at least one matrix-forming compound or said additive composition comprises:
        i) at least one compound selected from the group consisting of fatty acids, alcohol derivatives from fatty acids, monoglycerides, diglycerides, lipids and their derivatives, the corresponding compounds that have their acid group(s) replaced by a hydroxyl or thiol or ether or thioether group or ω-hydroxyalkenes or their ethers or homologous thiols or thioethers; monoacylglycerols, cis monounsaturated monoacylglycerols, monoolein (C18: c9), monopalmitolein (C16: c9) and monovacennin (C18: c7); medium-chain length alkyl glycosides; polyalkylenglycols, polyethylenglycols, diacylglycerophospholipids, monoacylglycerophospholipids and derivatives thereof capable of forming a crystallization matrix for the membrane protein; and/or
        ii) at least one compound selected from the group consisting of polyketides, saccharelipids, prenol lipids, sterol lipids, sphingolipids, glycerophospholipids and glycerolipids and/or derivates of lipids, phosphatidylcholine (PC), DOPC, phosphatidylethanolamine, DOPE, phosphatidylserine, DOPS, cardiolipin, lysophosphatidylcholine, 2-monoolein, oleamide, cholesterol, cell membrane components, and natural or synthetic compounds stabilizing the membrane protein in the crystallization matrix.

6. A method for manufacturing a crystallization device comprising multiple receptacles with a pre-defined amount of at least one matrix-forming compound capable of forming a crystallization matrix for a membrane protein, wherein the method for manufacturing a clystallization device comprises the method for loading a crystallization device according to claim 1.

7. The method according to claim 1, wherein modifying the state of aggregation of said at least one matrix-forming compound comprises heating said at least one matrix-forming compound.

8. The method of claim 3, wherein the method is automated.

* * * * *